United States Patent
Chen et al.

(10) Patent No.: US 6,214,869 B1
(45) Date of Patent: *Apr. 10, 2001

(54) HETEROCYCLIC CIS CYCLOPROPANE DERIVATIVES AS MELATONERGIC AGENTS

(75) Inventors: Jie Chen, Madison, CT (US); Pierre Dextraze, Laprairie; Marco Dodier, Quebec, both of (CA); Katherine S. Takaki, Middletown, CT (US)

(73) Assignee: Bristol-Myers Squibb, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/318,033

(22) Filed: May 25, 1999

Related U.S. Application Data

(60) Provisional application No. 60/088,199, filed on Jun. 5, 1998.

(51) Int. Cl.[7] .................. A61K 31/36; A61K 31/343; C07C 233/05; C07D 307/79; C07D 317/48
(52) U.S. Cl. .................. 514/465; 514/469; 514/623; 514/624; 549/441; 549/467; 564/207
(58) Field of Search .................. 514/469, 465, 514/623, 624; 549/467, 441; 564/207

(56) References Cited

U.S. PATENT DOCUMENTS

| 5,753,709 | 5/1998 | Keavy et al. |
| 5,856,529 | 1/1999 | Catt et al. |

FOREIGN PATENT DOCUMENTS

| 48729/93 | 10/1993 | (AU) |
| 420 064 | 4/1991 | (EP) |
| 506 539 | 9/1992 | (EP) |
| 527 687 | 2/1993 | (EP) |
| 562 956 | 9/1993 | (EP) |
| 708 099 | 4/1996 | (EP) |
| WO 94/07487 | 4/1994 | (WO) |
| WO 95/17405 | 6/1995 | (WO) |
| WO 95/29173 | 11/1995 | (WO) |
| WO 97/43272 | 11/1997 | (WO) |

OTHER PUBLICATIONS

Arendt, J., et al., "Alleviation of Jet Lag by Melatonin: Preliminary Results of Controlled Double Blind Trail", *Br. Med. J.*, 292, pp. 1170–1172 (May 1986).

Cassone, V. M., et al., "Dose–Dependent Entrainment of Rat Circadian Rhythms by Daily Injection of Melatonin", *J. Biol. Rhythms*, 1, (3), pp. 219–229 (1986).

Reppert, S. M., et al., "Cloning and Characterization of a Mammalian Melatonin Receptor That Mediates Reproductive and Circadian Responses", *Neuron*, 13, pp. 1177–1185 (Nov., 1994).

Reppert, S. M., et al., "Molecular Characterization of a Second Melatonin Receptor Expressed in Human Retina and Brain: The $Mel_{1b}$ Melatonin Receptor", *Proc. Natl. Acad. Sci. USA*, 92, pp. 8734–8738 (Sep. 1995).

*Primary Examiner*—Joseph K. McKane
*Assistant Examiner*—Taofiq A. Solola
(74) *Attorney, Agent, or Firm*—Aldo A. Algieri

(57) ABSTRACT

There is provided a novel series of cis cyclopropane compounds of Formula I

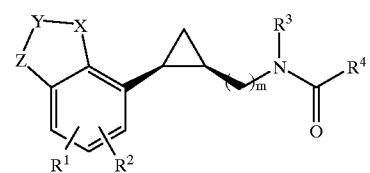

wherein $R^1$, $R^2$, $R^3$, $R^4$, X, Y, Z and m are as defined herein which bind to the human melatonin receptor and therefore are useful as melatonergic agents.

10 Claims, No Drawings

HETEROCYCLIC CIS CYCLOPROPANE DERIVATIVES AS MELATONERGIC AGENTS

CROSS REFERENCE TO RELATED APPLICATION

This application claims the benefit of provisional application U.S. Ser. No. 60/088,199 filed Jun. 5, 1998.

BACKGROUND OF THE INVENTION

The present invention pertains to novel substituted heterocyclic cis cyclopropane derivatives having drug and bio-affecting properties and to their preparation, pharmaceutical formulations and use. In particular, the invention concerns benzodioxoles, benzofurans, dihydrobenzofurans, dihydrobenzodioxanes and related derivatives bearing aminoalkyl substituted cis cyclopropane groups. These compounds possess melatonergic properties that should make them useful in treating certain medical disorders.

Melatonin (N-acetyl-5-methoxytryptamine) is a hormone which is synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

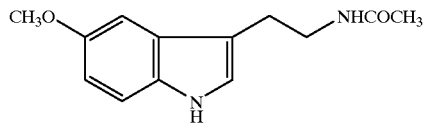

Melatonin

Recent evidence demonstrates that melatonin exerts its biological effects through specific receptors. Use of the biologically active, radiolabelled agonist $[^{125}I]$-2-iodomelatonin has led to the identification of high affinity melatonin receptors in the CNS of a variety of species. The sequences of two cloned human melatonin receptors have been reported [Reppert, et al., *Proc. Natl. Acad. Sci.* 92, p. 8734–8738, (1995) and Reppert, et al., *Neuron* 13, p. 1177–1185, (1994)]. In mammalian brain, autoradiographic studies have localized the distribution of melatonin receptors to a few specific structures. Although there are significant differences in melatonin receptor distribution even between closely related species, in general the highest binding site density occurs in discreet nuclei of the hypothalamus. In humans, specific $[^{125}I]$-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms,* 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487, published on Apr. 14, 1994.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, premenstrual syndrome, immune disorders, inflammatory articular diseases and neuroendocrine disorders.

Aside from simple indole derivatives of melatonin itself, various bicyclic structures have been prepared and their use as melatonin ligands disclosed. In general these bicyclic amide structures can be represented as:

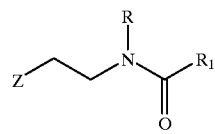

wherein Z is an aryl or heteroaryl system attached by a two carbon bridge to the amide group. Some specific examples follow.

Yous, et al. in European Patent Application EP-527,687A, published on Feb. 17, 1993, disclose as melatonin ligands arylethylamines i,

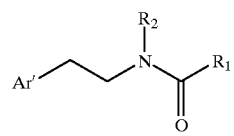

i wherein Ar' is, inter alia, a substituted or unsubstituted benzo[b]thiophen-3yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Yous, et al. in European Patent Application EP-506,539A, published on Sep. 30, 1992, claim ligands ii,

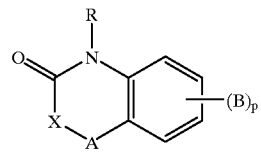

ii wherein A is oxygen or sulfur; X is a methylene group or a bond; and R is H or lower alkyl when p is 1 and B is defined by the radical iii,

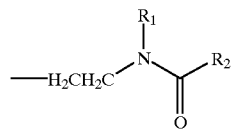

wherein $R_1$ is hydrogen or lower alkyl and $R_2$ is, inter alia, hydrogen, lower alkyl or cycloalkyl. Alternatively, R is defined by the radical iii when p is 0 or 1 and B is lower alkoxy.

Several naphthalene derivatives have also been disclosed as melatonin ligands.

Yous, et al. in European Patent Application EP-562,956A, published on Sep. 29, 1993, disclose amide and urea naphthalene derivatives iv,

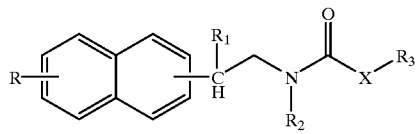

in which R is hydrogen or $OR_4$ wherein $R_4$ is, inter alia, hydrogen, alkyl, cycloalkyl, or cycloalkylalkyl; $R_1$ is hydrogen or $COOR_5$ wherein $R_5$ is hydrogen or alkyl; $R_2$ is hydrogen or alkyl; X is NH or a bond; and $R_3$ is, inter alia, alkyl, alkenyl, or cycloalkyl.

Langlois, et al., in Australian Patent Application AU-A-48729/93 disclose arylalkyl(thio)amides v as melatonergic ligands,

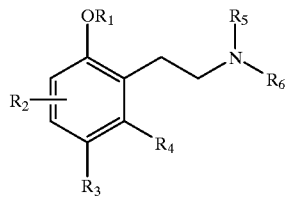

wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl or $R_3$ and $R_4$, together with the benzene ring which carries them, form a ring-system $E_3$ chosen from, inter alia, naphthalene, on the understanding that the portion of the ring-system $E_3$ formed by $R_3$ and $R_4$ and the two carbon atoms of the benzene ring which carry them is unhydrogenated or partially hydrogenated; $R_5$ is hydrogen or lower alkyl; and $R_6$ is,

wherein X is sulfur or oxygen and $R_7$ is, inter alia, lower alkyl or alkenyl.

Compound vi is included as a specific example,

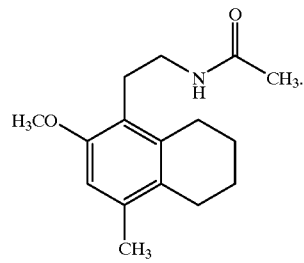

Horn and Dubocovich in European Patent Application EP-420,064A, published on Apr. 3, 1991, disclose 2-amidotetralins vii as melatonin ligands,

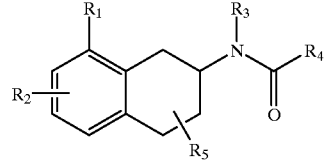

wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Lesieur et al, in EP-708,099A, published Apr. 24, 1996, disclose compounds of structure viii, which are useful for the treatment of diseases caused by a melatonin imbalance.

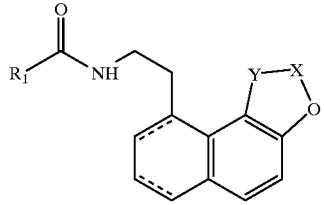

wherein ——— is a single or double bond; $R_1$=Me or MeNH; and X—Y=—CH(Me)—CH$_2$—, CH$_2$CH(OH)— or (CH$_2$)$_3$—.

North et al., in International Application WO 95/29173, published Nov. 2, 1995, disclose naphthalene derivatives of structure ix:

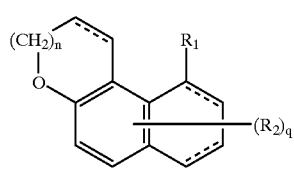

wherein $R_1$ is a group of the formula $CR_3R_4$ $(CH_2)_p NR_5$ $COR_6$; $R_2$ is hydrogen, halogen, $C_{1-6}$ alkyl, $OR_7$ or $CO_2R_7$; and may be the same or different substituent when q is 2; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; $R_7$ is hydrogen or $C_{1-6}$ alkyl; n is zero, 1 or 2; p is an integer of 1, 2, 3 or 4; q is 1 or 2; and the dotted lines indicate the absence or presence of an additional bond. The North et al. compounds are taught to treat chronobiological disorders.

In International Application WO 95/17405, published on Jun. 29, 1995, North et al., disclose compounds of structure x and teach their use in the treatment of conditions related to the melatonin system.

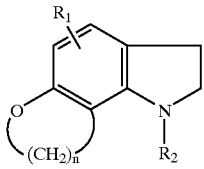

x wherein $R_1$ is hydrogen, halogen or $C_{1-6}$ alkyl; $R_2$ is a group of formula $-CR_3R_4(CH_2)_pNR_5COR_6$; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; n is an integer of 2, 3 or 4; and p is an integer of 1, 2, 3 or 4.

Keavy, et al., in U.S. Pat. No. 5,753,709, issued on May 19, 1998, disclose compounds of formula xi which are useful as melatonergic agents,

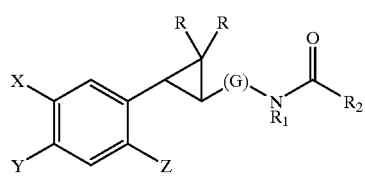

xi wherein X represents halogen, hydrogen, $C_{1-4}$alkyl or $OR_5$ wherein, inter alia, $R_5$ is hydrogen, $C_{1-20}$alkyl or $C_{4-20}$alkylcycloalkyl; Y represents hydrogen or halogen; X represents inter alia, hydrogen, halogen, cyano or aryl; R represents hydrogen, halogen or $C_{1-4}$alkyl or; $R_1$ represents hydrogen, $C_{1-4}$alkyl or benzyl and $R_2$ represents $C_{1-6}$alkyl, $C_{2-6}$alkenyl, $C_{3-6}$cycloalkyl, $C_{2-4}$alkoxyalkyl, $C_{1-4}$trifluoromethylalkyl or $C_{2-8}$alkylthioalkyl.

In International Application WO 97/43272, published on Nov. 20, 1997, Ellis, et al., disclose compounds of structure xii as melatonin ligands.

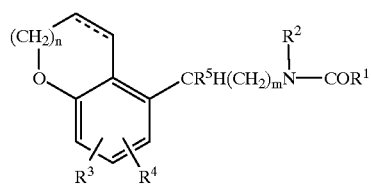

xii wherein $R^1$ and $R^2$ present hydrogen, $C_{1-6}$alkyl, $C_{3-7}$cycloalkyl or aryl, $R^3$ and $R^4$ represent hydrogen, halogen or $C_{1-6}$alkyl or substituted aryl, $R^5$ represents hydrogen or $C_{1-6}$alkyl, n is 0–2, m is 1–4 and the dotted line represents an additional bond.

The foregoing disclosures do not teach or suggest the novel melatonergic benzodioxole, benzofuran or dihydrobenzofurans of the present invention. The novel compounds of the present invention display melatonergic agonist activity.

SUMMARY OF THE INVENTION

The invention provides a novel series of cis cyclopropane compounds of Formula I

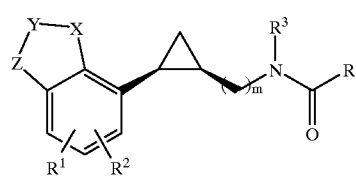

I wherein $R^1$, $R^2$, $R^3$, $R^4$, X, Y, Z and m are as defined below, including hydrates and solvates thereof which bind to the human melatonergic receptor and therefore are useful as melatonergic agents in the treatment of sleep disorders, seasonal depression, shifts in circadian cycles, melancholia, stress, appetite regulation, benign prostatic hyperplasia and related conditions.

DETAILED DESCRIPTION OF THE INVENTION

The invention provides a novel series of cis cyclopropane compounds of Formula I and solvates thereof having the formula:

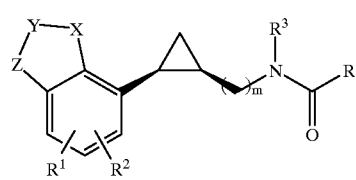

I wherein
$R^1$ and $R^2$ each are independently hydrogen or halogen;
X is $CH_2$, CH or oxygen;
Y is $CR^5$, $CR^5R^6$ or $(CH_2)_n$, with n=1–2;
Z is $CH_2$, CH or oxygen;
m is 1 or 2;
$R^3$ is hydrogen or $C_{1-4}$ alkyl;
$R^4$ is $C_{1-6}$ alkyl, $C_{3-6}$ cycloalkyl, $C_{1-3}$ haloalkyl, $C_{2-6}$ alkenyl, $C_{1-4}$ alkoxy($C_{1-4}$)alkyl, $C_{1-4}$ alkylthio($C_{1-4}$) alkyl or $C_{1-4}$ trifluoromethylalkyl; and
$R^5$ and $R^6$ each are independently hydrogen or $C_{1-4}$ alkyl.

The present invention also provides a method for the treatment of sleep disorders and related conditions, which comprises administering a therapeutically effective amount of a compound of Formula I or a solvate or hydrate thereof.

$R^1$ and $R^2$ are selected from H and halogen (i.e., bromine, chlorine, iodine or fluorine). It is most preferred that $R^1$ and $R^2$ be H.

X may be $CH_2$, CH (when a double bond is present) or oxygen.

Y is $CR^5$ (when a double bond is present), $CR^5R^6$ or $-(CH_2)_n-$ and n is preferably 1 or 2.

Z may be $CH_2$, CH (when a double bond is present) or oxygen, with oxygen being most preferred.

When X and Y are $CH_2$ and Z is oxygen or Z and Y are $CH_2$ and X is oxygen, the compound is a dihydrobenzofuran. When X and Y are CH and Z is oxygen or Z and Y are CH and X is oxygen, the compound is a benzofuran. When X and Z are oxygen and Y is $CH_2$, the compound is a benzodioxole. When X and Z are oxygen and Y is $(CH_2)_2$, the compound is a benzodioxane. Compounds in which X and Y are $CH_2$ and Z is oxygen are preferred.

m is 1 or 2, with m=1 preferred.

$R^4$ is one of several types of groups. $R^4$ is selected from $C_{1-6}$ alkyl, $C_{3-6}$ cycloalkyl, $C_{1-3}$ haloalkyl, $C_{2-6}$ alkenyl, $C_{1-4}$ alkoxy($C_{1-4}$)alkyl, $C_{1-4}$ trifluoromethylalkyl and $C_{1-4}$ alkylthio($C_{1-4}$)alkyl groups. $R^1$ is preferably $C_{1-6}$ alkyl or $C_{3-6}$ cycloalkyl.

$R^3$ is hydrogen or $C_{1-4}$ alkyl. $R^3$ is preferrably hydrogen.

$R^5$ and $R^6$ are hydrogen or $C_{1-4}$ alkyl. It is preferred that $R^5$ and $R^6$ both be hydrogen. It is also preferred that $R^5$ is hydrogen and $R^6$ is methyl. When $R^5$ is hydrogen and $R^6$ is methyl, both enantiomers and racemate are preferred.

"Alkyl" means a monovalent straight or branched chain group of the formula $C_xH_{2x+1}$, with x being the number of carbon atoms.

"Alkenyl" means a straight or branched hydrocarbon radical containing a carbon-carbon double bond.

"Y—X" and "Y—Z" refer to a single bond or double bond attachment when defined by the substituents X, Y, and Z.

"Cycloalkyl" groups are monovalent cyclic moieties containing at least 3 carbon atoms and conforming to the formula $C_xH_{(2x-1)}$, with x being the number of carbon atoms present. The cyclopropyl group is a preferred cycloalkyl moiety.

"Haloalkyl" includes straight and branched chain hydrocarbon radicals bearing from 1 to 3 halogen moieties. "Halogen" means F, Cl, Br or I. Preferred halogens in haloalkyl moieties of $R^4$ include F and Cl.

One group of preferred compounds include the benzofurans and dihydrobenzofurans of Formula I wherein the group, —X—Y—Z—, consists of —$CH_2$—$CH_2$—O—, —CH=CH—O—, —$CH_2$—C($CH_3$)$_2$—O—, —$CH_2$—CH($CH_3$)—O— and —CH=$CCH_3$—O—.

Some preferred compounds of this group include:
(cis)-N-[[2-(2,3-dihydrobenzofuran-4-yl)cycloprop-1-yl]methyl]propanamide;
(cis)-N-[[2-(2,3-dihydrobenzofuran-4-yl)cycloprop-1-yl]methyl]acetamide;
(cis)-N-[[2-(2,3-dihydrobenzofuran-4-yl)cycloprop-1-yl]methyl]cyclopropane carboxamide;
(cis)-N-[[2-(2,3-dihydrobenzofuran-4-yl)cycloprop-1-yl]methyl]butyramide; and
(cis)-N-[[2-(2,3-dihydrobenzofuran-4-yl)cycloprop-1-yl]methyl]-2-methyl propanamide.

Another group of preferred compounds include the benzodioxoles and benzodioxanes of Formula I wherein the group, —X—Y—Z—, consists of —$CH_2$—O— and —O—($CH_2$)$_2$—O—, respectively.

Still another group of preferred compounds include the benzopyrans of Formula I wherein the group, —X—Y—Z, consists of —$CH_2$—($CH_2$)$_2$—O—.

Additionally, compounds of Formula I encompass all pharmaceutically acceptable solvates, particularly hydrates, thereof. The present invention also encompasses diastereomers as well as optical isomers, e.g. mixtures of enantiomers including racemic mixtures, as well as individual enantiomers and diastereomers, which arise as a consequence of structural asymmetry in certain compounds of Formula I. Separation of the individual isomers or selective synthesis of the individual isomers is accomplished by application of various methods which are well known to practitioners in the art.

Compounds of Formula I can be prepared using the overall processes and many of several modifications shown in the following Reaction Scheme:

Reaction Scheme 1

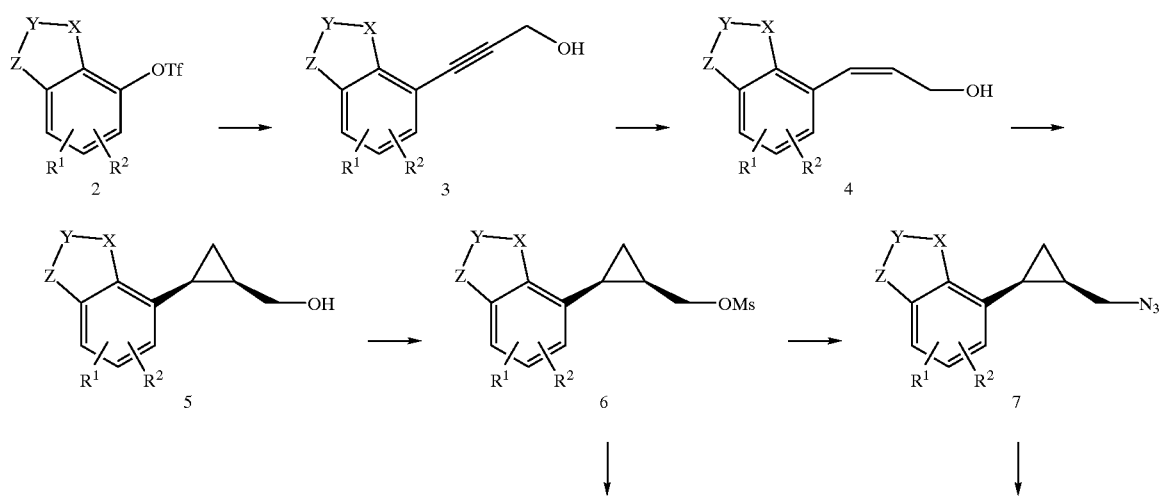

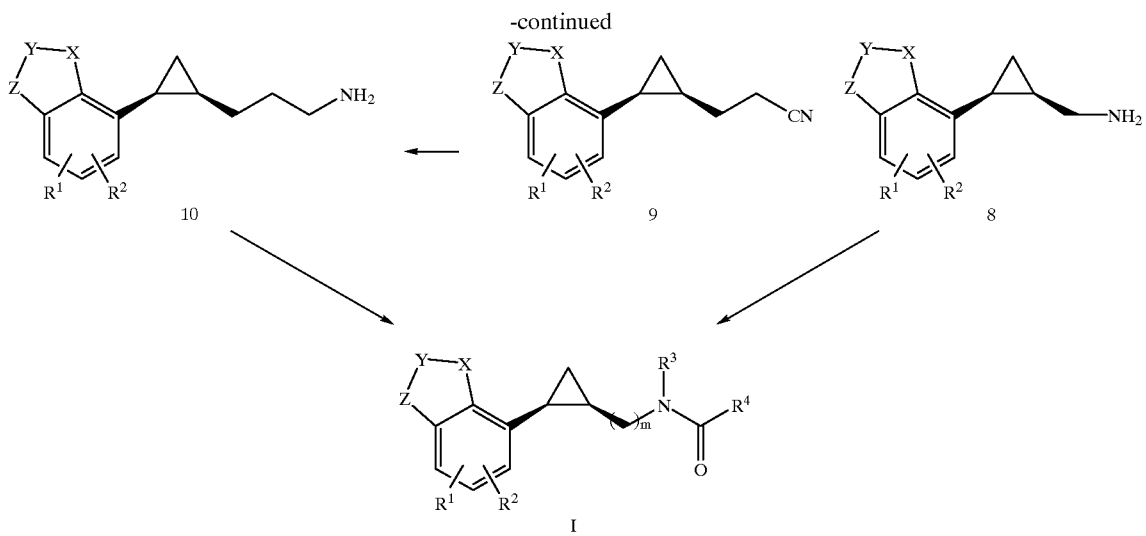

The starting triflates of Formula 2 can be prepared by methods well known to those skilled in the art from the corresponding phenols. Conversion to the acetylenic alcohols of Formula 3 can be accomplished by palladium-mediated coupling to propargylic alcohol using a Pd catalyst like tetrakis(triphenylphosphine)palladium (0), palladium (II) acetate, dichlorobis(triphenylphosphine)palladium (II), and the like in the presence of a co-catalyst like copper iodide and a base like diisopropylamine in an inert solvent such as tetrahydrofuran or dimethylformamide. Reduction of the triple bond to the cis olefins of Formula 4 can be accomplished by catalytic hydrogenation using palladium catalysts such as palladium on carbon in pyridine or Lindlar's catalyst. The cis olefin of Formula 4 can be converted to the cyclopropanes of Formula 5 using Simmons-Smith conditions such as treatment of diiodomethane with Zn—Cu couple or treatment of a dihalomethane with $Et_2Zn$ in solvents such as ether or methylene chloride. The cyclopropyl alcohols of Formula 5 can then be converted to the amines of Formulas 8 and 10 by first forming the mesylates of Formula 6 with methane sulfonyl chloride and an acid scavenger, followed by displacement of the mesylate with sodium azide and reduction of the azides of Formula 7 with lithium aluminum hydride to provide the penultimate amines of Formula 8 or by displacement with sodium cyanide to give the compound of Formula 9, followed by reduction of the nitrile group with a reducing agent, such as LAH, to provide the penultimate amines of Formula 10. Further reaction of amines of Formulas 8 or 10 with acylating reagents provides compounds of Formula I. Suitable acylating agents include carboxylic acid halides, anhydrides, acyl imidazoles, alkyl isocyanates, alkyl isothiocyanates and carboxylic acids in the presence of condensing agents such as carbonyl imidazole, carbodiimides, and the like.

Biological Activity of the Compounds

The compounds of the invention are melatonergic agents. They have been found to bind human melatonergic receptors expressed in a stable cell line with good affinity. Further, the compounds are agonists as determined by their ability, like melatonin, to block the forskolin-stimulated accumulation of cAMP in certain cells. Due to these properties, the compounds and compositions of the invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia, benign prostatic hyperplasia, inflammatory articular diseases, headaches, and related conditions.

Melatonergic Receptor Binding Activity

1. Reagents:
   (a) TME=50 mM Tris buffer containing 12.5 mM $MgCl_2$, and 2 mM EDTA, pH 7.4 at 37° C. with concentrated HCl.
   (b) Wash buffer: 20 mM Tris base containing 2 mM $MgCl_2$, pH 7.4 at room temperature.
   (c) $10^{-4}$ M melatonin ($10^{-5}$ M final concentration).
   (d) 2-[$^{125}$I]-iodomelatonin, 0.1 M final concentration 2. Membrane Homogenates:

The melatonin $ML_{1a}$ receptor cDNA was subcloned into pcDNA3 and introduced into NIH-3T3 cells using Lipofectamine. Transformed NIH-3T3 cells resistant to geneticin (G-418) were isolated, and single colonies expressing high levels of 2[$^{125}$I]-iodomelatonin binding were isolated. Cells are maintained in DMEM supplemented with 10% calf serum and G-418 (0.5 g/liter). Cells are grown to confluency in T-175 flasks, scraped using Hank's balanced salt solution, and frozen at −80° C. For preparing membrane homogenates, pellets are thawed on ice, and resuspended in TME buffer in the presence of 10 μg/ml aprotinin and leupeptin, and 100 μM phenylmethylsulfonylfluoride. The cells were then homogenized using a dounce homogenizer, and centrifuged. The resulting pellet was resuspended with dounce homogenizer in TME (supplemented with the above protease inhibitors) and frozen. On the day of assay, the small aliquot was thawed on ice and resuspended in ice cold TME (1:50–1:100 v/v) and held on ice until assayed.

3. Incubation: 37° C. for 1 hour. Reaction is terminated by filtration. Filters are washed 3 times.

4. References: Reppert, et al., *Neuron*, 13, p. 1177–1185 (1994).

TABLE 1

| Example No. | Melatonin Binding Affinity (IC$_{50}$)[a] |
|---|---|
| 1 | ++ |
| 2 | + |
| 3 | ++ |
| 4 | ++ |
| 5 | ++ |

[a] = (IC$_{50}$) values for ML$_{1a}$ human melatonin receptor binding
++ = <50 nM
+ = 50–200 nM The compounds of the present invention have affinity for receptors of the endogenous pineal hormone, melatonin, as determined in a receptor binding assays described above in Table 1 for the ML$_{1a}$ (human) receptors. Melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer, benign prostatic hyperplasia, immune disorders and neuroendocrine disorders.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

In making pharmaceutical compositions containing compounds of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The dosage of the compounds of Formula I to achieve a therapeutic effect will depend not only on such factors as the age, weight and sex of the patient and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

The compositions are preferably formulated in a unit dosage form, each dosage containing from about 0.1 to 100 mg, more usually 1 to 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 10 mg/day, in single or divided doses, is preferred. Generally, the compounds of the invention may be used in treating sleep and related disorders in a manner similar to that used for melatonin.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The compounds which constitute this invention, their methods of preparation and their biologic actions will appear more fully from consideration of the following examples, which are given for the purpose of illustration only and are not to be construed as limiting the invention in sphere or scope.

DESCRIPTION OF SPECIFIC EMBODIMENTS

In the following examples, used to illustrate the foregoing synthetic processes, all temperatures are expressed in degrees Celsius and melting points are uncorrected. Proton magnetic resonance ($^1$H NMR) and carbon magnetic resonance ($^{13}$C NMR) spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. The infrared (IR) spectral descriptions include only absorption wave numbers ($cm^{-1}$) having functional group identification value. The IR determinations were employed using the compound neat as a film or by employing potassium bromide (KBr) as diluent. Optical rotations $[\alpha]_D^{25}$ were determined in the solvents and concentration indicated. Low resolution mass spectra (MS) are reported as the apparent molecular weight $(M+H)^+$. The elemental analyses are reported as percent by weight.

Preparation of Intermediates of Formula 2
2,3-Dihydrobenzofuran-4-yl)trifluoromethane sulfonate
Step 1: 2-Bromoresorcinol

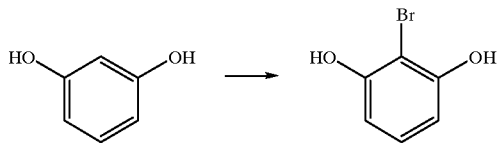

Bromine (0.363 L) was added dropwise over 2 hours to a solution of resorcinol (250 g) in dichloromethane (3.5 L). The solution was stirred at room temperature for 18 hours at which time approximately 1 L of the dichloromethane was removed by distillation. MeOH was added and the distillation continued in this manner until all of the dichloromethane was removed and the solution contained approximately 1.5 L of MeOH. To this was added a solution of NaOH (181.5 g) and $Na_2SO_3$ (573 g) in $H_2O$ (7.5 L). The resulting mixture was stirred at ambient temperature for 1 hour. The solution was then acidified to pH=2 with concentrated HCl (75 mL) and extracted with tert-butyl methyl ether (TBME) (2×1 L). The combined organic layers were treated with activated charcoal (20 g) and filtered through Celite; the Celite was washed with an additional 500 mL of TBME. The solvent was then removed in vacuo. The resulting crude 2-bromoresorcinol was dissolved in a minimum amount of ethyl acetate and filtered through silica gel eluting with a gradient from 20% to 40% ethyl acetate in hexanes yielding 2-bromoresorcinol (122 g). m.p. 86–88°.

Step 2: 2,6-Di(2-chloroethoxy)bromobenzene

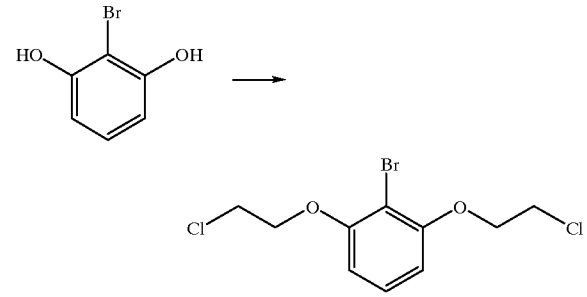

Potassium carbonate (536 g), sodium iodide (9.76 g), and sodium metabisulfate (12.2 g) were suspended in dichloromethane (1.53 L) and DMF (0.4 L) and heated to 80° C. A solution of 2-bromoresorcinol (122.3 g) in DMF (0.4 L) was then added dropwise over 2 hours. The reaction was stirred at 80° C. for 20 hours, cooled to ambient temperature and filtered through a medium porosity fritted funnel. The solid residue was washed with DMF (2×0.28 L) and organic fractions combined. The organics were washed with 1N HCl (1×1.84 L and 1×0.92 L), half-saturated $NaHCO_3$ solution (0.92 L), half-saturated brine (0.92 L), dried over $Na_2SO_4$ and concentrated in vacuo.

The crude product was dissolved in EtOH (142 mL) and TBME (76 mL) and treated with activated charcoal (14 g) at 70° C. for 0.25 hours. The suspension was filtered through Celite. The solution was cooled to 0° C. for 48 hours and the crystals collected (44.88 g). The mother liquor was concentrated and passed over a plug of silica gel eluting with 20% ethyl acetate in hexane yielding an additional 39.25 g of pure product. The total yield of title compound was 84.13 g, (41.4%).

Step 3: 2,3-Dihydro-4-hydroxybenzofuran

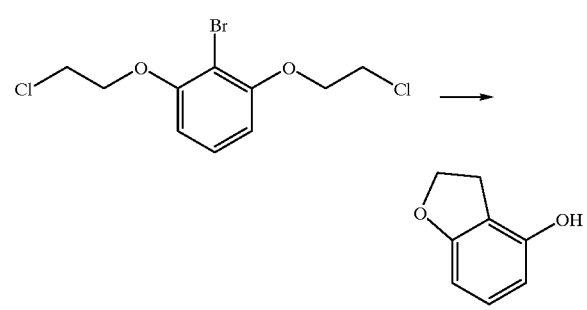

The product of Step 2 (39.25 g) was dissolved in THF (0.5 L) and cooled to −78° C. nBuLi (2.5M in hexanes, 300 mL) was then added dropwise over 30 minutes and the reaction stirred at −70° C. for an additional 45 minutes. The solution was then warmed to 0° C. over 10 minutes and stirred at this temperature for 1 hour. Glacial acetic acid (16 mL) was added followed by 1N NaOH (160 mL) and the layers allowed to separate. The organics were extracted with 1N NaOH (2×80 mL) and the combined aqueous fractions were then washed with TBME (160 mL). TBME (240 mL) was then added and the aqueous layer acidified with 6N HCl. The aqueous layer was re-extracted with TBME (240 mL), and the combined organics stirred over activated charcoal (5 g) for 15 minutes, filtered through Celite, and concentrated in vacuo. The crude product was crystallized from toluene and heptane to yield the title compound (16.8 g, 99%).

Step 4: 2,3-Dihydrobenzofuran-4-yl trifluoromethane sulfonate

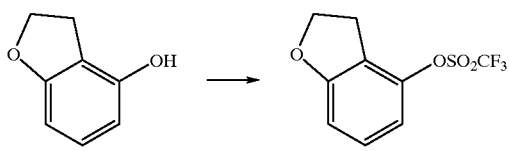

The product of Step 3 (1.0 g) was dissolved in anhydrous dichloromethane (5 mL) and cooled to 0° C. Pyridine (0.87 mL) was then added followed by dropwise addition over 30 minutes of trifluoromethansulfonic anhydride (2.28 g). Stirred from 0° C. to ambient temperature over 1 hour. The methylene chloride solution was then washed with water (2×4.6 mL), 10% phosphoric acid (4.6 mL), saturated NaHCO$_3$ solution (4.6 mL) and brine (2.3 mL). The solution was then treated with activated carbon (170 mg) for 5 minutes, filtered through Celite, dried over Na$_2$SO$_4$ and concentrated in vacuo to yield the title compound (1.74 g, 88%).

Preparation of Intermediates of Formula 3
3-(2,3-Dihydrobenzofuran-4-yl)prop-2-yn-1-ol A mixture of the triflate (0.1 mol), propargylic alcohol (0.2 mol), CuI (10 mmol), dichlorobis(triphenylphosphine) palladium (II) (5 mmol) and diisopropylamine (100 mL) in 300 mL of DMF was stirred at 80° C. for 15 h and then at RT for 4 days. The crude reaction mixture was then diluted with ether (300 mL) and washed sequentially with water (1×200 mL), 1N HCl (3×200 mL), saturated aqueous sodium bicarbonate solution (1×200 mL) and then brine (1×200 mL). The organic phase was separated, dried over magnesium sulfate, filtered and concentrated in vacuo to provide a brown oil. Purification by silica gel column chromatography (Hexanes:EtOAc, 4:1) provided 6.44 g (37%) of the desired product as a yellow-brown oil.

$^1$H NMR (300 MHz, CDCl$_3$) δ7.07 (t, J=7.8 Hz, 1H), 6.93 (d, J=7.6 Hz, 1H), 6.77 (d, J=7.9 Hz, 1H), 4.59 (t, J=8.8 Hz, 2H), 4.52 (s, 2H), 3.26 (t, J=8.7 Hz, 2H).

Preparation of Intermediates of Formula 4
(cis)-3-(2,3-Dihydrobenzofuran-4-yl)prop-2-en-1-ol A mixture of 3-(2,3-dihydrobenzofuran-4-yl)prop-2-yn-1-ol (6.2 mmol) and Pd/C (300 mg) in 20 mL of pyridine was shaken under an atmosphere of H$_2$ (10 psi) until no starting material remained (8 h). The crude reaction mixture was filtered to remove the catalyst and the catalyst was washed with ether. The filtrate was concentrated in vacuo to provide 1.1 g of the desired product as a yellow oil (quantitative yield).

$^1$H NMR (300 MHz, CDCl$_3$) δ7.11 (t, J=7.8 Hz, 1H), 6.74 (d, J=8.0 Hz, 1H), 6.68 (d, J=7.7 Hz, 1H), 6.48 (d, J=11.7 Hz, 1H), 5.89–5.97 (m, 1H), 4.59 (t, J=8.7 Hz, 2H), 4.42 (dd, J=6.4, 1.6 Hz, 2H), 3.15 (t, J=8.7 Hz, 2H).

Preparation of Intermediates of Formula 5
(cis)-2-(2,3-Dihydrobenzofuran-4-yl)cycloprop-1-yl methanol Diethylzinc (63 mmol, 1.0 M in hexanes) was added dropwise to a mixture of (cis)-3-(2,3-dihydrobenzofuran-4-yl)prop-2-en-1-ol (12.6 mmol) in 10 mL of CH$_2$Cl$_2$ at −15° C. The resulting mixture was stirred at −15° C. for 1 h followed by the dropwise addition of CH$_2$Cl$_2$ (63 mmol). The resulting mixture was warmed to RT and stirred overnight. The crude reaction mixture was then quenched with saturated aqueous NH$_4$Cl solution at 0° and extracted with ether (2×100 mL). The combined organic extracts were washed with saturated aqueous NH$_4$Cl solution, dried over magnesium sulfate, filtered and concentrated in vacuo. Purification by silica gel column chromatography (Hexanes:EtOAc, 4:1) provided 2.06 g (86%) of the desired product.

$^1$H NMR (300 MHz, CDCl$_3$) δ7.05 (t, J=7.9 Hz, 1H), 6.68 (d, J=7.9 Hz, 1H), 6.61 (d, J=7.7 Hz, 1H), 4.57–4.64 (m, 2H), 3.43–3.49 (m, 1H), 3.24–3.35 (m, 3H), 2.06–2.15 (m, 1H), 1.52–1.59 (m, 1H), 1.02–1.10 (m, 1H), 0.89–0.94 (m, 1H).

Preparation of Intermediates of Formula 6
(cis)-[2-(2,3-Dihydrobenzofuran-4-yl)cycloprop-1-yl] methyl methane sulfonate Methane sulfonyl chloride (6.5 mmol) was added dropwise to a solution of (cis)-2-(2,3-dihydrobenzofuran-4-yl) cycloprop-1-yl methanol (5.0 mmol) and triethylamine (7.5 mmol) in 50 mL of CH$_2$Cl$_2$ at 0° C. The resulting mixture was allowed to warm to RT and stirred for 2 h. The crude reaction mixture was then diluted with CH$_2$Cl$_2$ (50 mL) and washed sequentially with water (2×50 mL), saturated aqueous sodium bicarbonate solution (2×50 mL) and then brine (1×50 mL). The organic phase was separated, dried over magnesium sulfate, filtered and concentrated in vacuo to provide 1.38 g of the desired product as an oil (quantitative yield).

$^1$H NMR (300 MHz, CDCl$_3$) δ6.98 (t, J=7.8 Hz, 1H), 6.61 (d, J=7.9 Hz, 1H), 6.49 (d, J=7.7 Hz, 1H), 4.51–4.57 (m, 2H), 4.11 (dd, J=6.1, 10.5 Hz, 1H), 3.52–3.58 (m, 1H), 3.15–3.21 (m, 2H), 2.48 (s, 3H), 2.13–2.19 (m, 1H), 1.57–1.69 (m, 1H), 1.07–1.15 (m, 1H), 0.94–1.00 (m, 1H).

Preparation of Intermediates of Formula 7
(cis)-2-(2,3-Dihydrobenzofuran-4-yl)cycloprop-1-yl methyl azide A solution of (cis)-[2-(2,3-dihydrobenzofuran-4-yl) cycloprop-1-yl]methyl methane sulfonate (5.0 mmol) and sodium azide (10.0 mmol) in 100 mL of dimethylformamide was heated at 70° C. for 1 h. The reaction mixture was allowed to cool to room temperature and stirred overnight. The crude reaction mixture was then diluted with CH$_2$Cl$_2$ (100×mL) and washed sequentially with water (3×100 mL) and then brine (1×100 mL). The organic phase was separated, dried over magnesium sulfate, filtered and concentrated in vacuo to provide 1.1 g of the desired product as an oil (quantitative yield).

¹H NMR (300 MHz, CDCl₃) δ7.07 (t, J=7.8 Hz, 1H), 6.70 (d, J=7.9 Hz, 1H), 6.56 (d, J=7.6 Hz, 1H), 4.59–4.65 (m, 2H), 3.24–3.30 (m, 2H), 3.07 (dd, J=6.9, 13 Hz, 1H), 2.95 (dd, J=7.9, 13 Hz, 1H), 2.12–2.19 (m, 1H), 1.51–1.57 (m, 1H), 1.12–1.19 (m, 1H), 0.93–0.99 (m, 1H).

Preparation of Intermediates of Formula 8
(cis)-2-(2,3-Dihydrobenzofuran-4-yl)cycloprop-1-yl methyl amine A solution of (cis)-2-(2,3-dihydrobenzofuran-4-yl)cycloprop-1-yl methyl azide (5.0 mmol) in 20 mL of tetrahydrofuran was added dropwise to a mixture of lithium aluminum hydride (10.0 mmol) in 40 mL of tetrahydrofuran at −40° C. The resulting mixture was allowed to warm to RT and stirred overnight. The crude reaction mixture was quenched by the sequential addition of water (1.0 mL), 10 N sodium hydroxide (1.0 mL) and water (3.0 mL). The solid material was removed by filtration through Celite and the filtrate was concentrated in vacuo. The resulting residue was dissolved in ether (100 mL) and washed with brine (50 mL). The organic phase was separated, dried over magnesium sulfate, filtered and concentrated in vacuo to provide 630 mg of the desired product as an oil (66%).

¹H NMR (300 MHz, CDCl₃) δ7.04 (t, J=7.8 Hz, 1H), 6.67 (d, J=7.9 Hz, 1H), 6.57 (d, J=7.7 Hz, 1H), 4.55–4.63 (m, 2H), 3.22–3.29 (m, 2H), 2.38–2.52 (m, 2H), 2.01–2.07 (m, 1H), 1.35–1.45 (m, 3H), 0.98–1.05 (m, 1H), 0.81–0.87 (m, 1H).

EXAMPLE 1
(cis)-N-[[2-(2,3-Dihydrobenzofuran-4-yl)cycloprop-1-yl]methyl]propanamide A solution of (cis)-2-(2,3-dihydrobenzofuran-4-yl)cycloprop-1-yl methyl amine (0.43 mmol), triethylamine (1.30 mmol) and propionyl chloride (0.65 mmol) in 10 mL of methylene chloride was stirred at room temperature overnight. The reaction mixture was washed with brine (2×20 mL). The organic phase was separated, dried over magnesium sulfate, filtered and concentrated in vacuo. Purification by silica gel column chromatography (Hex:EtOAc, 4:1) provided 23 mg of the desired product (22%) as a yellow oil. HPLC purity >95%.

¹H NMR (300 MHz, CDCl₃) δ7.04 (t, J=7.8 Hz, 1H), 6.67 (d, J=7.9 Hz, 1H), 6.57 (d, J=7.6 Hz, 1H), 5.27 (br s, 1H), 4.56–4.64 (m, 2H), 3.12–3.33 (m, 2H), 2.98–3.04 (m, 2H), 2.12 (q, J=7.6 Hz, 2H), 2.00–2.18 (m, 1H), 1.42–1.55 (m, 1H), 1.09 (t, J=7.6 Hz, 3H), 0.99–1.21 (m, 1H), 0.86–0.92 (m, 1H);

¹³C NMR (75 MHz, CDCl₃) δ173.7, 160.0, 135.4, 128.2, 127.4, 119.5, 107.8, 71.2, 39.7, 29.9, 29.2, 18.8, 18.0, 10.0, 8.5;

IR (neat) 1643, 1548, 1235 cm⁻¹; MS (ESI) m/e 246 (M+H)⁺.

EXAMPLE 2
(cis)-N-[[2-(2,3-Dihydrobenzofuran-4-yl)cycloprop-1-yl]methyl]acetamide The title compound was prepared by the general procedure described in Example 1 using (cis)-2-(2,3-dihydrobenzofuran-4-yl)cycloprop-1-yl methyl amine (0.79 mmol), triethylamine (2.37 mmol) and acetyl chloride (0.95 mmol). Purification by silica gel column chromatography (Hex:EtOAc, 1:1) provided 92 mg of the desired product (50%) as an off-white wax. HPLC purity=93%.

¹H NMR (300 MHz, CDCl₃) δ6.97 (t, J=7.8 Hz, 1H), 6.59 (d, J=7.9 Hz, 1H), 6.49 (d, J=7.7 Hz, 1H), 5.28 (br s, 1H), 4.46–4.58 (m, 2H), 2.94–3.25 (m, 3H), 2.79–2.88 (m, 1H), 1.94–2.04 (m, 1H), 1.83 (s, 3H), 1.34–1.47 (m, 1H), 0.92–1.00 (m, 1H), 0.77–0.81 (m, 1H);

¹³C NMR (75 MHz, CDCl₃) δ170.0, 159.9, 135.2, 128.1, 127.3, 119.5, 107.7, 71.1, 39.8, 29.0, 23.4, 18.7, 17.8, 8.4;

IR (KBr) 3329, 1648, 1557, 1236 cm⁻¹; MS (ESI) m/e 232 (M+H)⁺.

EXAMPLE 3
(cis)-N-[[2-(2,3-Dihydrobenzofuran-4-yl)cycloprop-1-yl]methyl]cyclopropane carboxamide The title compound was prepared by the general procedure described in Example 1 using (cis)-2-(2,3-dihydrobenzofuran-4-yl)cycloprop-1-yl methyl amine (0.79 mmol), triethylamine (2.37 mmol) and cyclopropane carbonyl chloride (0.95 mmol). Purification by silica gel column chromatography (Hex:EtOAc, 2:1) provided 88 mg of the desired product (43%) as a white wax. HPLC purity=92%.

¹H NMR (300 MHz, CDCl₃) δ7.02 (t, J=7.8 Hz, 1H), 6.65 (d, J=8.0 Hz, 1H), 6.56 (d, J=7.7 Hz, 1H), 5.45 (br s, 1H), 4.45–4.62 (m, 2H), 3.12–3.33 (m, 2H), 2.97–3.04 (m, 2H), 1.99–2.07 (m, 1H), 1.44–1.54 (m, 1H), 1.15–1.21 (m, 1H), 0.98–1.05 (m, 1H), 0.85–0.92 (m, 3H), 0.64–0.70 (m, 2H);

¹³C NMR (75 MHz, CDCl₃) δ173.4, 159.8, 135.3, 128.1, 127.4, 119.4, 107.6, 71.1, 39.9, 29.1, 18.7, 17.9, 14.8, 8.4, 7.1;

IR (KBr) 3323, 1639, 1558, 1238 cm⁻¹; MS (ESI) m/e 258 (M+H)⁺.

EXAMPLE 4
(cis)-N-[[2-(2,3-Dihydrobenzofuran-4-yl)cycloprop-1-yl]methyl]butyramide The title compound was prepared by the general procedure described in Example 1 using (cis)-2-(2,3-dihydrobenzofuran-4-yl)cycloprop-1-yl methyl amine (0.79 mmol), triethylamine (2.37 mmol) and butyryl chloride (0.95 mmol). Purification by silica gel column chromatography (Hex:EtOAc, 2:1) provided 61 mg of the desired product (30%) as a white solid. HPLC purity=98%. m.p. 73–74°;

¹H NMR (300 MHz, CDCl₃) δ6.97 (t, J=7.8 Hz, 1H), 6.59 (d, J=8.0 Hz, 1H), 6.50 (d, J=7.7 Hz, 1H), 5.19 (br s, 1H), 4.46–4.59 (m, 2H), 3.02–3.26 (m, 2H), 2.85–3.02 (m, 2H), 1.94–2.01 (m, 3H), 1.46–1.61 (m, 2H), 1.36–1.46 (m, 1H), 0.90–0.99 (m, 1H), 0.84 (t, J=7.3 Hz, 3H), 0.78–0.87 (m, 1H);

¹³C NMR (75 MHz, CDCl₃) δ172.8, 159.9, 135.3, 128.1, 127.3, 119.4, 107.6, 71.1, 39.6, 38.8, 29.0, 19.2, 18.7, 17.9, 13.8, 8.4;

IR (KBr) 3312, 1640, 1554, 1237 cm⁻¹; MS (ESI) m/e 260 (M+H)⁺.

EXAMPLE 5
(cis)-N-[[2-(2,3-Dihydrobenzofuran-4-yl)cycloprop-1-yl]methyl]-2-methyl propanamide The title compound was prepared by the general procedure described in Example 1 using (cis)-2-(2,3-dihydrobenzofuran-4-yl)cycloprop-1-yl methyl amine (0.79 mmol), triethylamine (2.37 mmol) and isobutyryl chloride (0.95 mmol). Purification by recrystallization from EtOAc/Hexanes provided 76 mg of the desired product (37%) as colorless plates. HPLC purity>98%. m.p. 125–126°;

¹H NMR (300 MHz, CDCl₃) δ6.97 (t, J=7.8 Hz, 1 H), 6.59 (d, J=7.9 Hz, 1H), 6.50 (d, J=7.7 Hz, 1H), 5.17 (br s, 1H), 4.46–4.59 (m, 2H), 3.04–3.26 (m, 2H), 2.92–2.97 (m, 2H), 2.16 (septet, J=6.9 Hz, 1H), 1.94–2.01 (m, 1H), 1.34–1.47 (m, 1H), 1.01 (dd, J=2.2, 6.9 Hz, 6H), 0.93–1.06 (m, 1H), 0.80–0.85 (m, 1H);

¹³C NMR (75 MHz, CDCl₃) δ176.7, 159.9, 135.3, 128.1, 127.2, 119.3, 107.6, 71.1, 39.5, 35.7, 29.1, 19.6, 18.6, 17.9, 8.4;

IR (KBr) 3309, 1640, 1553, 1238 cm⁻¹; MS (ESI) m/e 260 (M+H)⁺.

We claim:

1. A cis cyclopropane compound of Formula I having the formula:

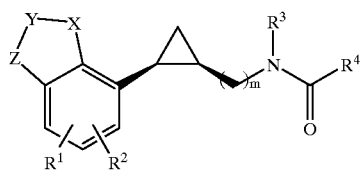

wherein
R¹ and R² each are independently hydrogen or halogen;
X is CH₂, CH or oxygen;
Y is CR⁵, CR⁵R⁶ or (CH₂)ₙ, with n=1–2;
Z is CH₂, CH or oxygen;
m is 1 or 2;
R³ is hydrogen or C₁₋₄ alkyl;
R⁴ is C₁₋₆ alkyl, C₃₋₆ cycloalkyl, C₁₋₃ haloalkyl, C₂₋₆ alkenyl, C₁₋₄ alkoxy(C₁₋₄)alkyl, C₁₋₄ alkylthio(C₁₋₄)alkyl or C₁₋₄ trifluoromethylalkyl; and
R⁵ and R⁶ each are independently hydrogen or C₁₋₄ alkyl.

2. A compound of claim 1 wherein R³ is hydrogen and m is 1.

3. A compound of claim 2 wherein R⁴ is C₁₋₆ alkyl or C₃₋₄ cycloalkyl.

4. A compound of claim 3 wherein X is CH₂ and Z is oxygen.

5. A compound of claim 4 selected from the group consisting of:
(cis)-N-[[2-(2,3-dihydrobenzofuran-4-yl)cycloprop-1-yl]methyl]-propanamide;
(cis)-N-[[2-(2,3-dihydrobenzofuran-4-yl)cycloprop-1-yl]methyl]acetamide;
(cis)-N-[[2-(2,3-dihydrobenzofuran-4-yl)cycloprop-1-yl]methyl]cyclopropane carboxamide;
(cis)-N-[[2-(2,3-dihydrobenzofuran-4-yl)cycloprop-1-yl]methyl]butyramide; and
(cis)-N-[[2-(2,3-dihydrobenzofuran-4-yl)cycloprop-1-yl]methyl]-2-methyl propanamide.

6. The compound of claim 5 which is (cis)-N-[[2-(2,3-dihydrobenzofuran-4-yl)cycloprop-1-yl]methyl] propanamide.

7. A composition useful for treating sleep disorders comprising a therapeutic amount of a compound of claim 1 and a suitable amount of a pharmaceutically acceptable carrier.

8. A composition useful for treating circadian rhythm-related disorders comprising a therapeutic amount of a compound of claim 1 and a suitable amount of a pharmaceutically acceptable carrier.

9. A method of treating sleep disorders in a patient in need of such treatment comprising administering to said patient a therapeutic amount of a compound of claim 1.

10. A method of treating circadian rhythm-related disorders in a patient in need of such treatment comprising administering to said patient a therapeutic amount of a compound of claim 1.

* * * * *